United States Patent
Shepard

(10) Patent No.: US 6,635,679 B2
(45) Date of Patent: Oct. 21, 2003

(54) METHODS AND COMPOSITIONS FOR INACTIVATING VIRUSES

(75) Inventor: Scot R. Shepard, Clayton, NC (US)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/855,634

(22) Filed: May 14, 2001

(65) Prior Publication Data

US 2002/0169214 A1 Nov. 14, 2002

(51) Int. Cl.[7] .............................................. A61K 31/13
(52) U.S. Cl. ....................................... 514/663; 514/908
(58) Field of Search ................................. 514/663, 908

(56) References Cited

U.S. PATENT DOCUMENTS

| | | | |
|---|---|---|---|
| 4,481,189 A | * | 11/1984 | Prince |
| 5,186,945 A | | 2/1993 | Shanbrom |
| 5,614,405 A | | 3/1997 | Eibl et al. |
| 6,355,684 B1 | * | 3/2002 | Squires ...................... 514/643 |

FOREIGN PATENT DOCUMENTS

| | | |
|---|---|---|
| WO | 92/16201 | 10/1992 |
| WO | 97/02028 | 1/1997 |
| WO | 97/07674 | 3/1997 |
| WO | 98/42373 | 10/1998 |
| WO | 02/092139 | 11/2002 |

OTHER PUBLICATIONS

McCutcheon's vol. 1: Emulsifiers and Detergents, North America Ed. 2000, p 298.*

Davis et al. Microbiology, $2^{nd}$ Ed., 1973, pp. 1430–1433.*

* cited by examiner

Primary Examiner—Theodore J. Criares
(74) Attorney, Agent, or Firm—William P. Ramey, III

(57) ABSTRACT

The present invention relates to methods and processes of inactivating a viral contaminants in a biological source material or process intermediate by contacting the biological source material (e.g., a host cell, cell supernatant, cell lysate, blood plasma, tissue homogenate, or other biological materials) with a solution containing one or more alkylamine compounds. In a particular embodiment, the active ingredients are amphipathic, charged amines or amine oxides coupled to saturated hydrocarbon chains of varying lengths.

1 Claim, No Drawings

METHODS AND COMPOSITIONS FOR INACTIVATING VIRUSES

TECHNICAL FIELD OF THE INVENTION

The present invention relates to methods and compositions for inactivating viruses present in samples/process streams of biological origin.

BACKGROUND OF THE INVENTION

It is desirable to use biological materials as sources for medicinal and industrial intermediates and products. Due to the very nature of the biological materials or their methods of production, biological materials may contain unwanted agents of viral origin that may be pathological or otherwise undesirable. The intended end-use of materials derived from biological sources may require a reduction in the biological activity of viral agents known to be present, or that are potentially present, in the source material or process additives.

Reduction of viral activity in materials is commonly accomplished by a number of techniques including the use of heat, steam, pressure, chemical treatments and other methods. However, these techniques may irreversibly alter the properties of the biological source material or the desired substances to be obtained from same. In such cases, gentle, non-denaturative and specific methods are required to reduce the biological activity of viruses without damaging the desired molecules or substances of interest.

Prior methods known in the art for inactivation of viruses in labile process streams include photochemical treatments in the presence of Psoralens, solvent-detergent treatments (U.S. Pat. No. 4,481,189), caprylic acid treatments (U.S. Pat. No. 4,939,176), the use of UVC radiation (Vitex Technologies, formerly NY Blood Center), ultra short time heating (Charm Technologies, charmbio.com), photodynamic inactivation in presence of phenothiazine dyes (U.S. Pat. No. 4,534,972), and the use of low-molecular-weight electrophilic agents that bind to nucleic acids (Vitex, Inactine product 4 patents).

SUMMARY OF THE INVENTION

The present invention relates to methods and processes of inactivating a viral contaminants in a biological source material or process intermediate. The process of the present invention involves contacting the biological source material (e.g., a host cell, cell supernatant, cell lysate, blood plasma, tissue homogenate, or other biological materials) containing a biomolecule (e.g., a recombinant or native protein, lipid, nucleic acid, or carbohydrate) of interest with a solution containing one or more alkylamine compounds. In a particular embodiment, the active ingredients are amphipathic, charged amines or amine oxides coupled to saturated hydrocarbon chains of varying lengths. In a preferred embodiment, the one or more active ingredients used are selected from the group consisting of dimethyldecylamine, dimethyltridecylamine, dimethylundecylamine, dimethyldidecylamine, dimethyltetradecylamine, dimethylhexadecylamine, dimethyldecylamineoxide, dimethylundecylamineoxide, dimethyldidecylamineoxide, dimethytetradecylamineoxide and dimethyltridecylamineoxide. These compounds may be used at concentrations ranging from 0.001% up to their solubility limit in the given solution. Preferably, the concentration of the active ingredients ranges from 0.005% to 5%, 0.1% to 2%, or is approximately 0.5% of the total solution (weight basis).

The pH of the solution can range from pH 2 to pH 12. Preferably, the solution is at a pH ranging from pH 5.0 up to pH 8.0. More preferably, the pH ranges from pH 5.5 to 7.4, from pH 6 to 7.4, from pH 7.0 to 7.4, or is approximately pH 7.2.

The inactivation of the viral contaminants with the active ingredient of the invention can be carried out at a temperature of from about 2° C. to about 50° C. Preferably, the temperature is from about 2° C. to about 30° C., 2° C. to about 20° C., 2° C. to about 10° C., about 4° C., about 25° C., or at room temperature.

The biological source material may be blood plasma, other biological tissues or a recombinant source material such as transformed or transfected "host cells". "Host cells" are cells containing a biomolecule of interest. A "biomolecule of interest" is any biomolecule present in the biological source material or the host cells that one desires to isolate, purify, or formulate for subsequent processing or application. The biological source material may be blood, blood plasma, animal tissues, plant tissues or recombinant host cells or host cell extracts. The host cells may be of any type, preferably mammalian, bacterial, yeast, fungal, plant, avian, insect, or reptilian.

DETAILED DESCRIPTION OF THE INVENTION

The present invention relates to a process for the facile and non-denaturative inactivation of viruses present or potentially present in biological source materials. The process includes contacting the source material with certain charge-modified hydrocarbons under appropriate solution conditions.

In a particular embodiment, solution conditions are adjusted by sedimentation of an insoluble source material, for example, recombinant host cells producing a recombinant protein of interest, followed by re-suspension, or by solution exchange using filtration methods, by direct modification of the existing solution conditions, or by other means of solvent exchange. Source materials suspended or co-dissolved in the appropriate solution are then contacted with certain amphipathic molecules that cause the inactivation of biological agents. Agents that may be inactivated in this way include bacteria, yeast, fungi, mycoplasma, mammalian cells, other animal cells and lipid enveloped viruses, for example, viruses of the families Flaviviridae (BVDV) Retroviridae (HIV, MuLV), Togaviridae (SFV), Rhabdoviridae (VSV), Herpesviridae (CMV).

In a preferred embodiment, a biological source material containing a retrovirus, or suspected of containing a retrovirus, for example human immunodeficiency virus (HIV) or murine leukemia virus (MuLV) is contacted with dimethylamine and/or dimethylamine oxide compounds with alkyl chains of varying length, depending on microbe or virus type and solution conditions.

The alkyldimethylamines or alkyldimethylamine oxides do not denature individual lipid molecules or other molecules such as nucleic acids, proteins, carbohydrates, or small molecules such as organic acids, vitamins, etc. Thus, the alkyldimethylamines or alkyldimethylamine oxides are particularly suitable for the reduction of viral or microbial contaminants without the denaturation or destruction of the biomolecule of interest, such as a recombinant protein.

Once a biological source material has been obtained, it is contacted with the inactivation reagents of the present invention. The inactivation reagents comprise one or more active ingredients. In a particular embodiment, the one or more active ingredients are amphipathic, charged amines or amine oxides coupled to saturated hydrocarbon chains of varying lengths. In a preferred embodiment, the one or more active ingredients used are selected from the group consisting of dimethyldecylamine, dimethyltridecylamine, dimethylundecylamine, dimethyldidecylamine, dimethyltetradecylamine, dimethylhexadecylamine, dimethyldecylamineoxide, dimethylundecylamineoxide, dimethyldidecylamineoxide, dimethytetradecylamineoxide and dimethyltridecylamineoxide. Active ingredients may be used at concentrations ranging from 0.001% up to their solubility limit. Preferably, the concentration of the detergents ranges from 0.05% to 5%, 0.1% to 2%, or is approximately 1% of the total solution.

In addition to the one or more active ingredients, in a preferred embodiment, the biological source material may also be contacted with polyols, such as glycerol, to enhance the activity of the active ingredient or to protect the molecules of interest. Preferably, the glycerol concentration is at least 0.6%, or ranges from 0.6% to 20%, 0.6% to 12%, 0.6% to 6%, 0.6% to 3%, or 0.6% to 1%.

Preferably, the solution is at a pH ranging from pH 5.0 up to pH 8.0. More preferably, the pH ranges from pH 5.5 to 7.4, from pH 6 to 7.4, from pH 7.0 to 7.4, or is approximately pH 7.2.

The microbial and/or viral inactivation can be carried out at a temperature of from about 2° C. to about 50° C. Preferably, the temperature is from about 2° C. to about 30° C., 2° C. to about 20° C., 2° C. to about 10° C., about 4° C., about 25° C., or at room temperature.

The amount of time allowed for inactivation after contacting the biological source material with the inactivation reagent may be determined by one of skill in the art. For example, the biological source material may be incubated in the presence of the inactivation reagent for 40 minutes, 90 minutes, or 150 minutes. Shorter and longer times may also be appropriate. In general, the amount of time can be increased when the concentration of detergent is low and decreased when the amount of detergent is high. For example, an inactivation reagent with a 1% detergent concentration is effective after 40 minutes, while an inactivation reagent with a 0.1% detergent concentration should be incubated for 150 minutes or longer. For optimal inactivation, the exact amount of time necessary can be determined by a simple time-course experiment at a given concentration of active ingredient, where viability of the microbial or viral contaminant is determined over time. After a certain time point, no further decrease in viability will be observed. This time point is the optimal time necessary for inactivation.

Typically, if the biological source material is comprised of cells, the cells will lyse after contact with the inactivation reagent of the invention. After lysis of the cells, the solution can be centrifuged to collect cellular debris in the pellet, leaving the released protein or biomolecule of interest in the supernatant. The supernatant may be processed according to methods known to those of skill in the art to further isolate and purify the protein of interest. The methods utilized to further isolate and/or purify the protein of interest are highly dependent upon the characteristics and properties of the particular protein of interest, and must be determined for each protein.

This invention is further illustrated by the following example which should not be construed as limiting. The contents of all references, patents and published patent applications cited throughout this application are hereby incorporated by reference.

EXAMPLES

Inactivation of a Viral Contaminant in a Biological Source Material

Chinese hamster ovary (CHO) host cells are grown to 3×10-5 cell density and are then harvested from the reactor vessel. Cells are removed from the suspension to produce a clarified culture broth. Tetradecyldimethylamine is then added to the clarified culture broth to a concentration of 0.5% (w/w). The clarified culture broth is then incubated for a period of time during which membrane bound organisms and viruses are inactivated.

The same approach is taken for blood plasma, tissue extracts, and cell extracts. The amount of detergent, time of incubation, temperature of incubation, and other parameters are readily ascertained by those skilled in the art. Appropriate solution conditions and incubation times are identified and validated by the intentional addition, or "spike", of microbes or viruses of known titer into the biological source material prior to the addition of the charge-modified hydrocarbon. The charge-modified hydrocarbon is then added to the biological source material and samples are withdrawn at specific time points. The samples are then analyzed by appropriate methods, known to those skilled in the art, that measure the biological activity, growth characteristics, or infectivity of the microbe or virus initially "spiked" into the biological source material.

What is claimed is:

1. A method of inactivating a Murine Leukemia Virus (MuLV) in a biological source material with a solution comprising the step of contacting the biological source material with a solution comprising an effective amount of an active ingredient dimethytetradecylamineoxide.

* * * * *